United States Patent [19]

Seela

[11] Patent Number: 4,804,748
[45] Date of Patent: Feb. 14, 1989

[54] 7-DEAZA-2'-DEOXYGUANOSINE NUCLEOTIDES

[75] Inventor: Frank Seela, Paderborn, Fed. Rep. of Germany

[73] Assignee: Boehringer Mannheim GmbH, Mannheim, Fed. Rep. of Germany

[21] Appl. No.: 896,657

[22] Filed: Aug. 13, 1986

[30] Foreign Application Priority Data

Aug. 16, 1985 [DE] Fed. Rep. of Germany ....... 3529478

[51] Int. Cl.$^4$ .......................... C07H 19/14; C12P 1/00
[52] U.S. Cl. ........................................ 536/28; 536/24; 536/26; 536/27; 536/29
[58] Field of Search ............................................ 536/28

[56] References Cited

U.S. PATENT DOCUMENTS 3,321,463 5/1967 Moffatt ................................ 536/27
3,337,530 8/1967 Hanze .................................. 536/28

FOREIGN PATENT DOCUMENTS 0225696 8/1985 German Democratic Rep. ... 536/28

OTHER PUBLICATIONS

Winkeler, H-D. Seela F., J. Org. Chem., vol. 48, pp. 3119–3122, 1983.

Barr et al, Bio Techniques, vol. 4(5), pp. 428–432, 1986.

Mizusawa et al., Nucleic Acids Research, vol. 14(3) pp. 1319–1324, 1986.

Primary Examiner—Johnnie R. Brown
Assistant Examiner—L. Eric Crane
Attorney, Agent, or Firm—Felfe & Lynch

[57] ABSTRACT

The present invention provides 7-deaza-2'-deoxyguanosine nucleotides of the general formula:

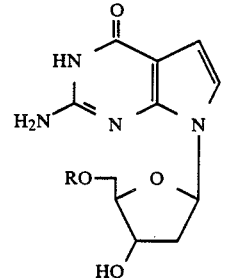

wherein R is a —PO$_3$H$_2$, —P$_2$O$_6$H$_3$ or —P$_3$O$_9$H$_4$ residue or an alkali metal, alkaline earth metal or ammonium salt of the phosphate groups. The present invention also provides processes for the preparation of these nucleotides and is also concerned with the use thereof in the sequencing of DNA.

2 Claims, No Drawings

7-DEAZA-2'-DEOXYGUANOSINE NUCLEOTIDES

FIELD OF THE INVENTION

The present invention is concerned with new 7-deaza-2'-deoxyguanosine nucleotides and with the use of such nucleotides for the preparation of sequences of nucleic acids.

BACKGROUND AND PRIOR ART

Several chemical methods for the sequencing of DNA are known, including the classic method of Maxam and Gilbert. Additionally, the enzymatic "plus-minus" method following Sanger and Coulson, *J. Mol. Biol.* 94: 441–448 (1975), is well known, and is used to elucidate nucleic acid sequences of DNA.

An alternative to the "plus-minus" method of Sanger and Coulson, supra, for sequencing of deoxyribonucleic acid (DNA) has been developed by Sanger, Nicklen, and Coulson, (*Proc. Nat. Acad. Sci. USA,* 74: 5463–5467 (1977). This method is based on the use of DNA polymerase-inhibiting nucleoside analogues. Since both arabinonucleotides, and in particular, 2',3'-dideoxynucleotides are used for this purpose, this method is also called the "dideoxy" method.

In the presence of DNA polymerase, 2',3'-dideoxynucleoside triphosphates are incorporated into growing oligonucleotide chains at the point of the "correct" nucleoside triphosphates. However, since these do not possess a 3'-hydroxyl group, the chain can not be further elongated after the first triphosphate has been incorporated. The chain growth terminates everywhere a 2',3'-dideoxy-nucleoside triphosphate is incorporated.

This effect is utilized for the sequencing of DNA by dividing a single strand DNA to be investigated into four samples (by e.g., enzymatic degradation, physical manipulation, and other techniques known to one skilled in the art). Each of these samples is incubated with a short, possibly radioactively-labelled DNA starter molecule in the presence of DNA polymerase, and three different deoxyribonucleoside triphosphates, one of which can be radioactively-labelled, and with a mixture of a fourth nucleoside triphosphate, which will differ in each of the four batches, and the appropriate 2',3'-dideoxynucleotide analogue. After the short start fragment has been hybridized on to the nucleic acid strand, the polymerase begins on the 3'-hydroxyl group of the "start" molecule with the synthesis of the molecule complementary to the DNA sequence to be investigated. The enzyme elongates this molecule until a 2',3'-dideoxy-nucleotide has been incorporated. Thereafter, after termination of the reaction and splitting off of the DNA strand serving as matrix by, e.g., denaturing, a mixture of fragments results which have the same 5' end in all four batches and all display the particular dideoxy analogue used as the 3' end. The gel electrophoretic separation of these molecules gives a band pattern for each batch which reproduces the distribution of the nucleotide corresponding to the particular nucleoside analogue in the newly synthesized DNA. By comparison of the band patterns of the four different batches, which are separated from one another on a gel, one can read off the sequence of the newly synthesized DNA directly. Further, since each nucleotide is complemented by only one other nucleotide, the sequence of the DNA strand serving as matrix can be determined as well.

The advantages of the dideoxy method are, in particular, the simplicity with which it can be carried out and avoidance of an additional incubation and purification step which is necessary in the case of the "plus-minus" method.

Problems arise not only in the case of the sequencing of nucleic acids according to the dideoxy method but also in the case of other sequencing methods which use DNA polymerase, particularly in the case of cytosine-guanine-rich regions. In single strand DNA, cytosine-guanine-rich sequences form stable loops due to internal base pairing. In the case of a gel electrophoretic separation of such fragments, this results in deficient resolution. Furthermore, guanine nucleotides are only moderately stable and, in aqueous solution, tend to form aggregates. This leads to difficulties in the enzymatic polymerization, since insufficient substrate is available on the active points of the enzyme. The result of this is that it is often difficult to sequence cytosine-guanine-rich regions in nucleic acids correctly, when using the dideoxy method.

Therefore, it is an object of the present invention to provide guanosine-nucleotide analogues which are stable, do not enter into self-aggregating units and can be used representatively for 2'-deoxyguanosine-nucleotides as substrate for DNA polymerase, e.g., in the sequencing of nucleic acids according to the dideoxy method.

SUMMARY OF THE INVENTION 7-deaza-2'-deoxyguanosine nucleotides according to the present invention of the general formula:

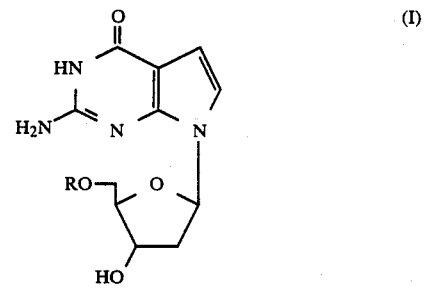

(I)

wherein R is a —PO$_3$H$_2$, —P$_2$O$_6$H$_3$, —P$_3$O$_9$H$_4$ residue or an alkali metal, alkaline earth metal, or ammonium salt of the phosphate groups.

Examples of alkali metal salts of the acid residues mentioned in the definition of R include lithium, sodium, and potassium salts. Alkaline earth metal salts in the acid residues mentioned in the definition of R include magnesium and calcium salts. Ammonium salts of the acid residues mentioned in the definition of R can contain unsubstituted ammonium ions or those which are substituted by alkyl radicals with up to 7 and preferably up to 4 carbon atoms, the triethyl- and tributylammonium ions being especially preferred. Substituents of the ammonium ions can also be aralkyl radicals, the benzyl radical here being preferred. The substituents of the ammonium ion can be the same or different.

The compounds of general formula (I) according to the present invention are new. They do not form aggregates which are typical for 2'-deoxy- or 2',3'-dideoxyguanosine derivatives. Furthermore, the triphosphate of general formula (I) is incorporated by DNA polymerase into growing DNA chains instead of 2'-deoxyguanosine triphosphate.

DETAILED DESCRIPTION OF PREFERRED EMBODIMENTS

The compounds of general formula (I) were prepared according to known methods from 7-deaza-2'deoxyguanosine, which can be prepared according to the method of Winkeler and Sella, (*J. Org. Chem.* 48: 3119–3122 (1983)).

By the reaction of 7-deaza-2'-deoxyguanosine with a phosphorylation agent, for example phosphorus oxychloride, in a trialkyl phosphate, preferably trimethyl phosphate, as solvent and subsequent working up, there can be obtained the 5'-monophosphates of the general formula:

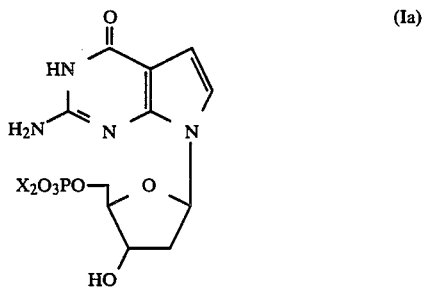

(Ia)

wherein X is a hydrogen atom or an alkali metal, alkaline earth metal or ammonium ion.

In the definition of X, the alkali metal, alkaline earth metal and ammonium ions have the same meanings as in the definition of R, supra.

Phosphorylation is preferably carried out at a low temperature and preferably at 0° to 10° C. The reaction time is from 5 hours to 1 day and preferably 7 to 15 hours.

Working up can take place, for example, by hydrolysis of the reaction mixture with ice, subsequent neutralization and isolation of the product by means of ion exchange chromatography.

The position of the phosphorylation can be determined by proton-decoupled $^{13}$C-NMR spectroscopy. The $^3$J(P-C) coupling constant of C-4', which is 8 Hz, can be used as indicator of the 0-5'-phosphorylation.

5'-Di- and 5'triphosphates of general formula (I) are prepared by activating a trialkylammonium salt of the 5'-monophosphate of general formula (Ia) and subsequently condensing with a trialkylammonium phosphate or diphosphate, the tributylammonium ion preferably being used as trialkylammonium ion. The activation advantageously takes place under anhydrous conditions by means of 1,1'-carbonyldiimidazole at ambient temperature in a polar, aprotic solvent, for example dimethylformamide. The condensation is also carried out at ambient temperature in a polar, aprotic solvent, dimethylformamide being preferred. The reaction times for the activating and condensation reaction each amount to from 3 hours to 3 days.

The success of the phosphorylation can be monitored by $^{31}$P-NMR spectroscopy. Reference is here made to Table 1, infra, in which are listed the chemical shifts of the phosphorus signal of the triethylammonium salts of 7-deaza-2'deoxyguanosine mono-, di- and trophosphates.

A further subject of the present invention is the use of compounds of general formula (I) in the sequencing of nucleic acids.

7-deaza-2'-deoxyguanosine triphosphate can be used instead of 2'-deoxyguanosine triphosphate in those sequencing methods for DNA in which the use of DNA polymerase is necessary. However, the use in the dideoxy sequencing method according to Sanger (*Proc. Nat. Acad. Sci. USA* 74: 5463–5467 (1977), is especially preferred. While maintaining the other usual conditions, 2'-deoxyguanosine triphosphate can here be replaced by 7-deaza-2'-deoxyguanosine triphosphate.

Instead of 7-deaza-2-deoxyguanosine triphosphate, there can also be used the corresponding 5'-mono- or 5'-diphosphate if, by means of appropriate additional enzymes and substrates, it is ensured that these nucleotides can be converted in the incubation solution into the 5'-triphosphate. Thus, for example, the monophosphates of general formula (I) are converted into the triphosphates by means of nucleoside monophosphate kinase and ATP and the corresponding diphosphate by means of nucleoside diphosphate kinase and ATP.

If the 7-deaza-2'-deoxyguanosine nucleotides of the present invention are used in these sequencing methods, then no disturbances due to secondary exchange reactions between cytosine and guanine are observed. This results in a substantially better gel-electrophoretic separation of guanine-cytosine-rich sequence fragments.

Thus, by using the compounds according to the present invention, a disturbance-free sequencing of cytosine-guanine-rich nucleic acids is possible.

The following Examples are given for the purpose of illustrating the present invention, but do not limit the broad scope thereof:

EXAMPLE 1

2-Amino-7-(2'-deoxy-β-D-erythropentofuranosyl)-3,7-dihydro-4H-pyrrolo[2,3-d]pyrimidin-4-one 5'-monophosphate triethylammonium salt 100 mg. (375 μmole) 2-amino-7(2'-deoxy-β-D-erythropentofuranosyl)-3,7-dihydro-4H-pyrrolo[2,3-d]pyrimidin-4-one were treated at 4° C. for 10 hours in 1.5 ml. trimethyl phosphate with 75 μl. (827 μmole) phosphorus oxychloride. The mixture was subsequently hydrolyzed with ice, neutralized with 1M aqueous triethylammonium bicarbonate solution and the solvent thereafter removed in a vacuum. The residue was then dissolved in water, applied to a 40×2.5 cm. ion exchange column (DEAE-Sephadex, hydrogen carbonate form), washed with 500 ml. water and chromatographed with a linear gradient of 0.5M triethylammonium bicarbonate (1000 ml.) and water (1000 ml.). The main zone was eluted at a salt concentration of 0.45M. The appropriate fractions were collected and evaporated to dryness. The volatile salts were removed by again taking up in water and again evaporating to dryness. There was thus obtained an amorphous product (2820 A$_{259}$ units, 211 μmole) in 56% yield. UV (water) λ$_{max}$=259 nm (ε13400).

Phosphate determination: 0.93 mole phosphate/mole aglycone.

$^{13}$C-NMR (D$_2$O): δ=8.7 (CH$_3$), 38.8 (C-2'), 64.8 (C-5', broad), 72.2 (C-3'), 83.4 (C-1'), 85.9 (d, J=8 Hz, C-4').

EXAMPLE 2

2-Amino-7-(2'-deoxy-β-D-erythropentofuranosyl)-3,7-dihydro-4H-pyrrolo[2,3-d]pyrimidin-4-one 5'-diphosphate triethylammonium salt The compound prepared in Example 1 (1500 $A_{259}$ units, 112 μmole) was dissolved in 30 ml. water and applied to a cation exchange column (25×2 cm., pyridinium form) and eluted with 500 ml. water. The eluate was evaporated to dryness and mixed with 27 μl. (112 μmole) tributylamine. Water was removed by repeatedly taking up in anhydrous dimethylformamide and subsequently evaporating to dryness. The tributylammonium salt of the compound prepared in Example 1 thus obtained was then dissolved in 2 ml. anhydrous dimethylformamide and treated with 90 mg. (560 μmole) 1,1'-carbonyldiimidazole. The reaction mixture was stirred for 5 hours at ambient temperature. Excess 1,1'-carbonyldiimidazole was then destroyed with 35 μl. methanol. After 30 minutes, 560 μmole tribuylammonium phosphate in 6 ml. dimethylformamide were added thereto and the reaction mixture was stirred for 24 hours at ambient temperature. After removal of the solvent in a high vacuum, the residue was dissolved in water and applied to an ion exchange column (45×3.5 cm cellulose, bicarbonate form). The diphosphate was eluted with a linear gradient of water and 0.5M triethylammonium bicarbonate (in each case 1000 ml.) at about 0.3M salt concentration. After removal of the solvent and subsequent lyophilization, there was obtained a colorless amorphous product (950 $A_{259}$ units) in 64% yield.

UV (water) $\lambda_{max}$=259 nm (ε13400).

EXAMPLE 3

2-Amino-7-(2'-deoxy-β-D-erythropentofuranosyl)-3,7-dihydro-4H-pyrrolo[2,3-d]pyrimidin-4-one 5'-triphosphate triethylammonium salt The compound prepared in Example 1 (1340 $A_{259}$ units, 100 μmole) was dissolved in 10 ml. water, applied to a cation exchange column (25×2 cm. pyridinium form) and the column was washed with 500 ml water. The eluate was evaporated to dryness and mixed with 24 μl. (100 μmole) tributylamine. Water was removed by repeatedly taking up in anhydrous dimethylformamide and subsequently evaporating to dryness. The residue was then dissolved in 2 ml. dimethylformamide and mixed with 80 mg. (500 μmole) 1,1'-carbonyldiimidazole which was dissolved in 2 ml. dimethylformamide. The reaction mixture was stirred for 24 hours at ambient temperature. Excess 1,1'-carbonyldiimidazole was decomposed with 35 μl. methanol. Subsequently, treatment was carried out at ambient temperature with 500 μmole bis-triethylammonium pyrophosphate dissolved in 2 ml. dimethylformamide. After stirring for 2 days, the reaction mixture was evaporated to dryness in a vacuum. The residue was dissolved in water and applied to an anion exchange column (40×2.5 cm.; bicarbonate form). Elution with a linear gradient of 0.5M triethylammonium bicarbonate and water (in each case 100 ml.) gave, at a salt concentration of 0.4M, after evaporated to dryness, the triphosphate in the form of a colorless, amorphous solid (817 $A_{259}$ units) in 61% yield.

UV (water) $\lambda_{max}$=259 nm (ε13400).

TABLE 1

Chemical shift of the $^{31}$P-NMR signals of the triethylammonium salts of the compounds prepared in Examples 1, 2 and 3, measured in $H_2O/D_2O$ (3:1 v/v) which contains 100 mM EDTA

| compound prepared in | $P_\alpha$ | $P_\beta$ | $P_\gamma$ |
|---|---|---|---|
| Example 1 | +4.65 (s) | | |
| Example 2 | −9.93 (d, J = 23 Hz) | −5.92 (d, J = 23 Hz) | |
| Example 3 | −10.00 (d, J = 20 Hz) | −21.54 (t, J = 20 Hz) | −8.35 (d, J = 20 Hz) |

It will be suggested that the specification and examples are illustrative but not limitative of the present invention and that other embodiments within the spirit and scope of the invention will suggest themselves to those skilled in the art.

What is claimed is:

1. Compound of the formula 7-deaza-2'-deoxyguanosine 5'-triphosphate and alkali earth metal, alkali metal and ammonium salts thereof.

2. 7-deaza-2'-deoxyguanosine 5-'triphosphate.

* * * * *